United States Patent

Goralski

[11] 4,014,875
[45] Mar. 29, 1977

[54] PROCESS OF MAKING DI OR TRIBROMOMETHANESULFONAMIDES

[75] Inventor: Christian T. Goralski, Midland, Mich.

[73] Assignee: The Dow Chemical Company, Midland, Mich.

[22] Filed: Apr. 11, 1975

[21] Appl. No.: 567,455

Related U.S. Application Data

[62] Division of Ser. No. 326,609, Jan. 26, 1973, Pat. No. 3,892,743.

[52] U.S. Cl. .................. 260/247.1 R; 260/293.85; 260/326.82
[51] Int. Cl.² ...................................... C07D 265/30
[58] Field of Search ................ 260/247.1 R, 556 A, 260/293.85, 326.82

[56] References Cited

OTHER PUBLICATIONS

Morrison et al., "Organic Chemistry" 2nd ed. (1970), pp. 545, 635, 636, 537.
Farrar, "J. Chem. Soc." (1956), pp. 508–513.

*Primary Examiner*—Henry R. Jiles
*Assistant Examiner*—R. W. Ramsuer
*Attorney, Agent, or Firm*—Theodore Post; C. Kenneth Bjork

[57] ABSTRACT

This invention concerns dibromo- and tribromomethanesulfonamides of the formula

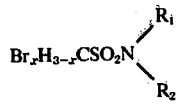

wherein

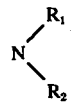

is a heterocyclic ring which may contain oxygen as another hetero atom and may be substituted with 1 to 2 lower alkyl groups, and $x$ is 2 or 3. The compounds have antimicrobial activity.

1 Claim, No Drawings

PROCESS OF MAKING DI OR TRIBROMOMETHANESULFONAMIDES

This is a division of application Ser. No. 326,609 filed Jan. 26, 1973 now U.S. Pat. No. 3,892,743.

SUMMARY OF THE INVENTION

This invention concerns dibromo- and tribromomethanesulfonamides corresponding to the formula

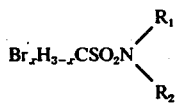

wherein $R_1$ and $R_2$ together with the nitrogen atom form a heterocyclic group which contains up to one hetero oxygen atom and may be substituted with 1 to 2 lower alkyl groups, such as, for example, a pyrrolidinyl, piperidinyl, morpholinyl, 4-methylpiperidinyl, or a 2,6-dimethylmorpholinyl group and $x$ represents 2 or 3. In the specification and claims, "lower alkyl" designates a 1 to 4 carbon atom straight or branched chain alkyl group, i.e., from 1, to 2, to 3, to 4 carbon atoms, such as, for example, methyl, ethyl, propyl, isopropyl, butyl, isobutyl or secondary butyl. The compounds are prepared by reacting a diamide of sulfoacetic acid with a large excess of bromine (6 to 10 mols/mol of diamide) in the presence of an aqueous solution of an alkali metal hydroxide, preferably sodium or potassium hydroxide, for a period of from 1–48 hours, preferably 24–48 hours, filtering off the solid products, and separating and purifying the products by fractional recrystallization from a suitable solvent, such as, for example, methanol or ethanol. The tribromomethanesulfonamides, being less soluble, crystallize out first; the dibromomethanesulfonamides, being more soluble, crystallize second. The starting diamides of sulfoacetic acid may be prepared by the method of Hoogenboom et al., J. Org. Chem., 34, 3414 (1969).

DESCRIPTION OF SOME PREFERRED EMBODIMENTS

The following examples describe representative specific embodiments and the best mode contemplated by the inventor of carrying out the invention. Temperature is given in centigrade degrees. The compounds are identified by elemental analysis and/or nuclear magnetic resonance spectroscopy.

EXAMPLE 1

(a) 2,6-Dimethyl-4-((tribromomethyl)sulfonyl)morpholine
(b) 2,6-Dimethyl-4-((dibromomethyl)sulfonyl)morpholine In a 250 ml. single-neck flask equipped with a magnetic stirrer are placed 1.67 g. (0.005 mol) of 4-((2,6-dimethylmorpholinosulfonyl)acetyl)-2,6-dimethylmorpholine, 100 ml. of aqueous 20% sodium hydroxide solution, 100 ml. of water, and 4.80 g. (0.03 mol) of bromine. The reaction mixture is allowed to stir at room temperature for 46 hours, after which time a white solid separates which is shown by nuclear magnetic resonance spectroscopy to be a mixture of the dibromo- and tribromo- title compounds. The solid is recrystallized from approximately 40 ml. of absolute ethanol to give 0.37 g. of crude 2,6-dimethyl-4-((tribromomethyl)sulfonyl)morpholine. Recrystallization of this material from approximately 7 ml. of absolute ethanol gives, after vacuum drying, 0.20 g. of pure 2,6-dimethyl-4-((tribromomethyl)sulfonyl)morpholine, m.p. 183°–184.5° C.

Anal. Calcd. for $C_7H_{12}Br_3NO_3S$: C, 19.55; H, 2.81; N, 3.26; S, 7.45. Found: C, 19.82; H, 2.79; N, 3.27; S, 7.61.

The crystallization liquor from the isolation of the crude 2,6-dimethyl-4-((tribromomethyl)sulfonyl)morpholine is concentrated and cooled in a freezer to give 0.53 g. of crude 2,6-dimethyl-4-((dibromomethyl)sulfonyl)morpholine. Recrystallization of this material from approximately 7 ml. of absolute ethanol gives, after vacuum drying, 0.24 g. of pure 2,6-dimethyl-4-((dibromomethyl)sulfonyl)morpholine, m.p. 105°–108° C.

Anal. Calcd. for $C_7H_{13}Br_2NO_3S$: C, 23.95; H, 3.73; N, 3.81; S, 9.15. Found: C, 23.61; H, 3.60; N, 3.81; S, 9.15.

EXAMPLE 2

Pursuant to the procedure of Example 1, the tribromomethanesulfonamides given in the following Table are prepared.

Table I

Amides of Tribromomethanesulfonic Acid

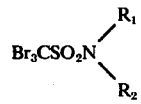

| | $R_1R_2N-$ | Mp, ° C. | Calcd C | Calcd H | Calcd N | Calcd S | Found C | Found H | Found N | Found S |
|---|---|---|---|---|---|---|---|---|---|---|
| a. | (piperidinyl) | 200–202 | 17.92 | 3.01 | 3.48 | 7.98 | 17.65 | 3.00 | 3.46 | not determined |
| b. | (morpholinyl) | 170–172 | 14.94 | 2.01 | 3.49 | 7.98 | 15.18 | 2.07 | 3.42 | 7.98 |

The corresponding dibromo compounds are separated from the above compounds following the procedure of Example 1.

The compounds of the invention are employed as antimicrobials for the control of bacteria, fungi and yeasts. For such uses, the compounds can be employed in an unmodified form or dispersed on a finely divided solid and employed as dusts. Such mixtures can also be dispersed in water with or without the aid of a surface-active agent and the resulting aqueous suspensions employed as sprays. In other procedures, the products can be employed as active constituents in solvent solutions, oil-in-water or water-in-oil emulsions or aqueous dispersions. The augmented compositions are adapted to be formulated as concentrates and subsequently diluted with additional liquid or solid adjuvants to produce the ultimate treating compositions. Good results are obtained when employing compositions containing antimicrobial concentrations and usually from about 100 to 10,000 parts by weight of one or more of the compounds per million parts of such composition.

In representative operations, compounds of the present invention were tested for their activity as antimicrobials using conventional agar dilution tests. The following Table presents results, expressed as concentration of toxicant in parts per million to achieve 100% growth inhibition (kills) of the indicated organisms.

Table II

| Compound of Example | Minimum Growth Inhibitory Concentration, ppm | | | | | | | | | | | | | |
|---|---|---|---|---|---|---|---|---|---|---|---|---|---|---|
| | Pa | Sa | Ca | Tm | Bs | At | Cp | Pp | St | Mp | Rn | Ci | Cf | Ts |
| 1 (a) | 100 | 500 | 100 | 100 | 100 | 10 | 100 | 100 | 100 | 100 | 100 | 100 | 100 | 100 |
| 1 (b) | — | — | 500 | 500 | * | 500 | 500 | 500 | — | — | 500 | — | 500 | — |
| 2 (b) | 100 | 500 | 100 | 100 | 100 | 100 | 100 | 100 | 100 | 100 | 100 | 100 | 100 | 100 |

Pa = P. aeruginosa
Pp = P. pullulans
Sa = S. aureus
St = S. typhosa
Ca = C. albicans
Mp = M. phlei
Tm = T. mentagrophytes
Rn = R. nigricans
Bs = B. subtilis
Ci = Ceratocystis ips
At = A. terreus
Cf = Cephaloascus fragans
Cp = C. pelliculosa
Ts = Trichoderm Sp. Madison P-42
— = not active at 500 ppm
* = 50% control at 500 ppm

What is claimed is:

1. A process for making dibromo- and tribromomethanesulfonamides by reacting a diamide of sulfoacetic acid having two $NR_1R_2$ amide groups wherein $NR_1R_2$ is a heterocyclic ring which may contain one oxygen atom and 1 to 2 lower alkyl substituent groups with excess bromine in the presence of aqueous alkali metal hydroxide and recovering product dibromo- and tribromomethanesulfonamide having the said $NR_1R_2$ amide group by fractional recyrstallization from a solvent in which the tribromomethanesulfonamide is less soluble than the dibromomethanesulfonamide.

* * * * *